United States Patent [19]

Hervé

[11] Patent Number: 4,927,267
[45] Date of Patent: May 22, 1990

[54] METHOD AND APPARATUS FOR OPTICALLY MEASURING, WITHOUT CONTACT, THE GRANULOMETRY OF A CLOUD OF PARTICLES OR THE ROUGHNESS OF A SURFACE

[75] Inventor: Philippe Hervé, Paris, France

[73] Assignee: Universite Paris X - Nanterre, Nanterre, France

[21] Appl. No.: 326,367

[22] Filed: Mar. 21, 1989

[51] Int. Cl.⁵ ............................................. G01N 21/47
[52] U.S. Cl. .................................... 356/336; 356/337; 356/338
[58] Field of Search ................................ 356/336, 338

[56] References Cited

U.S. PATENT DOCUMENTS

| | | | |
|---|---|---|---|
| 4,037,964 | 7/1977 | Wertheimer et al. | 356/336 |
| 4,037,965 | 7/1977 | Weiss | 356/336 |
| 4,052,600 | 10/1977 | Wentheimer | 356/336 X |
| 4,167,335 | 9/1979 | Williams | 356/336 |

*Primary Examiner*—Davis L. Willis
*Assistant Examiner*—Matthew W. Koren
*Attorney, Agent, or Firm*—Brumbaugh, Graves, Donohue & Raymond

[57] ABSTRACT

The invention relates to the measurement of the granulometry of a cloud of particles or of the roughness of a surface in real time and without contact, by means of an apparatus comprising: a convergent lens (9) adapted for forming a diffraction pattern of the cloud of particles or of the surface: multiplier means (10) adatped for multiplying this diffraction pattern, in intensity, by a function f(r) such that $$A(r^{1.5}+Br_o^4) < f(r) < A(r^4+Br_o^4)$$

with
A = constant determined by calibration of the apparatus
B = constant: $o < B < 0.1$
r = distance measured in the focal plane of the lens with respect to the optical axis thereof,
$r_o$ = maximum useful radius of the spatial filter, and means (11, 24) adapted for carrying out a reverse Fourier transform on the result of the above intensity multiplication, whose result forms the desired spectrum of the granulometry of the cloud of particles or the desired spectrum of the roughness of the surface.

10 Claims, 2 Drawing Sheets

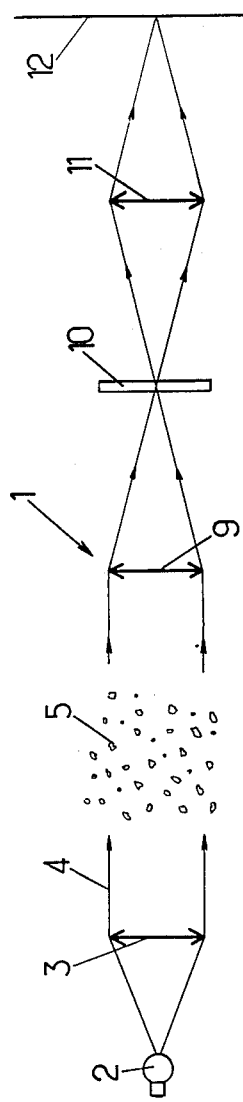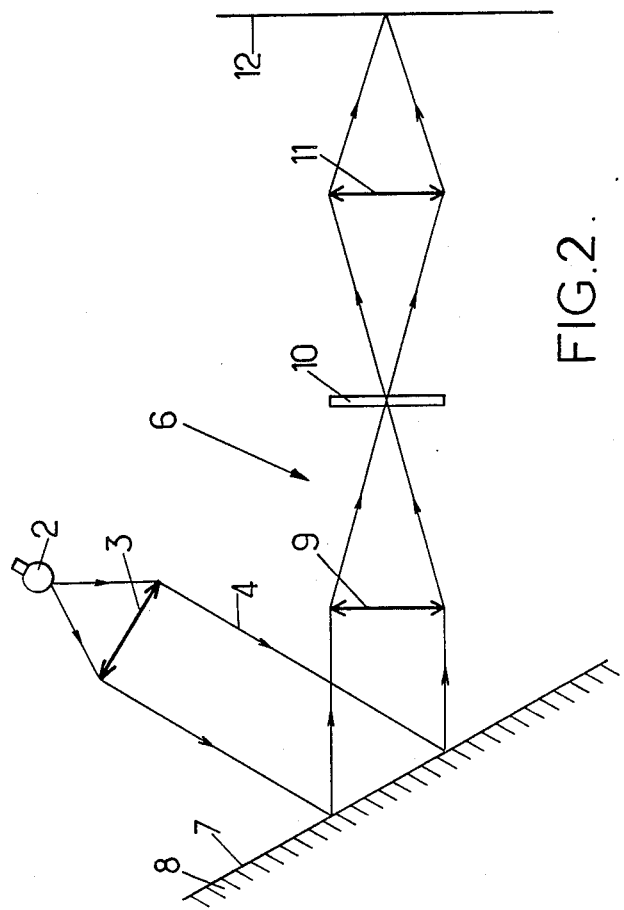

METHOD AND APPARATUS FOR OPTICALLY MEASURING, WITHOUT CONTACT, THE GRANULOMETRY OF A CLOUD OF PARTICLES OR THE ROUGHNESS OF A SURFACE

The present invention relates to the contactless measurement of the granulometry of a cloud of particles or of the roughness of a surface.

Numerous industrial applications, particularly in the fields of solar energy, pollution monitoring, heat insulation, space and military research, require the knowledge of the thermo-optical characteristics of materials such as emissivity, absorbtivity, reflectivity.

In particular, it may be necessary to determine these parameters for gas compositions or similar suspensions (e.g; characteristics of an aerosol, of a flame, etc. . . .).

By way of example, in so far as aerosols are concerned, the physiochemical characteristics are generally determined by causing the aerosol to deposit so as to obtain a liquid or a solid on which a certain number of well known measurements may then be made (in particular measurement of the Fresnel coefficients, of the emissivity, etc.). However, this way of proceeding is disadvantageous in many cases because more particularly of the sedimentation time which is long (several months for atmospheric fog); it is therefore impossible to follow up a chemical and/or physical evolution of a product, all the more so for monitoring a phenomenon with relatively rapid evolution.

Still by way of example, the optical measurements made on coal flames in an industrial boiler are the combination of two components: on the one hand, the natural emission of the flame which is representative to a certain extent of the operating conditions of the burner and, on the other hand, the emission and absorption of the cloud of fly ash enveloping the flames, a random component characteristic of the flow of gas in the boiler and, to a lesser extent, of the flames. Thus, improvement of combustion efficiency involves optimizing the granulometry of each type of pulverised coal, which requires a study of the granulometry of the flames. Up to now, the study of the granulometric distribution of the particle sizes is carried out by mechanical and/or electrical methods which require taking samples and which do not then allow the granulometry of the particles present in the flames to be characterized in situ and the evolution thereof to be followed in real time.

The object of the present invention is then essentially to overcome the drawbacks of presently known methods and to provide a method and apparatus for contactless measurement of the granulometry of a cloud of particles and so, consequently, measurement of the roughness of the surface of a body.

For these purposes, in a first of its aspects, the present invention provides a method for the contactless measurement of the granulometry of a cloud of particles or of the roughness of a surface, characterized in that:
a diffraction pattern is formed of the cloud of particles or of the surface of the body, by means of a convergent lens,
this diffraction pattern is multiplied, in intensity, by a function f(r) such that $$A(r^{1.5}+Br_o^4)<f(r)<A(r^4+Br_o^4)$$

with
A = constant determined by calibration
B = constant: $0<B<0.1$ r = distance measured in the focal plane of the lens with respect to the optical axis thereof,
$r_o$ = maximum useful radius of the spatial filter,
and a reverse Fourier transform is carried out on the result of this multiplication, whose result forms the desired spectrum of the granulometry of the cloud of particles or the desired spectrum of the roughness of the surface.

Thus, in accordance with the desired object, it is possible with the present invention to determine the granulometry of a cloud of particles or the roughness of a surface at a distance and without contact, therefore without disturbing the medium to be analysed, and possibly in real time, which makes possible a continuous analysis of an evolutive medium.

If required the function f(r) may be zero or less than the preceding value in the range $0<r<r_o/4$, i.e. outside the above defined range (case of an opaque central mask).

In a first embodiment of the method of the present invention, the multiplication in intensity of the diffraction pattern by the function f(r) and the reverse Fourier transform may be carried out using electronic computing means. Such mathematical computation is generally provided by means of a computer. The results thus obtained then have good accuracy but the procedure is relatively slow and does not make it possible to follow an evolutive phenomenon in real time. Furthermore, the equipment used is heavy, cumbersome and fragile. However, this solution may be chosen when accuracy of the result is required whereas a high analysis speed is not imperative.

In another embodiment of the present invention, the diffraction pattern is multiplied optically, in intensity, by an optical amplitude or phase spatial filter device situated in the image focal plane of said convergent lens, and in that the granulometry or roughness spectrum is formed optically by means of a second convergent lens whose object focal point is situated at the image focal point of the first convergent lens. This purely optical embodiment of the method of the present invention makes possible a continuous measurement in real time for following an evolutive phenomenon. Furthermore, another advantage of prime importance resides in the fact that the corresponding apparatus is a purely optical, relatively light, compact and robust apparatus (and in any case much lighter, much less cumbersome and more robust than the electronic equipment used for the first possible embodiment), which can for example be carried on board a vehicle, such as a missile or similar, while providing measurement accuracy which is satisfactory for most envisageable applications.

In a second of its aspects, the present invention provides an apparatus for contactless measurement of the granulometry of a cloud of particles or of the roughness of a surface, characterized in that it comprises:
a convergent lens (9) adapted for forming a diffraction pattern of the cloud of particles or of the surface,
multiplier means (10) adapted for multiplying this diffraction pattern, in intensity, by a function f(r) such that $$A(r^{1.5}+Br_o^4)<f(r)<A(r^4+Br_o^4)$$

with
A = constant determined by calibration of the apparatus

B = constant: $0 < B < 0.1$
r = distance measured in the focal plane of the lens with respect to the optical axis thereof,
$r_o$ = maximum useful radius of the spatial filter,
and means (11) adapted for carrying out a reverse Fourier transform on the result of the above intensity multiplication, whose result forms the desired spectrum of the granulometry of the cloud of particles or the desired spectrum of the roughness of the surface.

It is possible to use a central opaque mask, the function f(r) then being zero or less than the above mentioned value in the range $0 < r < r_o/4$, i.e. outside the above defined range.

It is possible to construct this apparatus in electronic form, by forming the intensity multiplying means and the means providing the reverse Fourier transform as electronic computers.

However, for numerous applications in which it is desirable to make measurements in real time so as to be able to follow an evolutive phenomenon and where a light and compact apparatus is desired, the means providing the reverse Fourier transform comprise a second convergent lens disposed so that its object focal point is situated at the image focal point of the first lens, and the intensity multiplier means comprise an optical amplitude spatial filtering device situated at the image focal point of the first lens and at the object focal point of the second lens, whereby, when the apparatus receives electromagnetic radiation having passed through the cloud of particles or been reflected by the surface, the spectrum of the granulometry of the cloud of particles or of the roughness of the surface is formed in the image focal plane of the second lens.

In one embodiment of a purely optical apparatus, the optical filtering device is a filter whose opacity decreases the further it is removed from the optical axis of the system.

In another embodiment of this apparatus, the optical filtering device is an opaque mask whose area between two radii r and r+dr increases so that the intensity passing through the corresponding ring increases in accordance with the above mentioned law f(r).

The present invention will be better understood from the following detailed description of two preferred embodiments given solely by way of non limitative examples, with reference to the accompanying drawings in which:

FIG. 1 shows very schematically the construction of an optical apparatus in accordance with the present invention for measuring the granulometry of a cloud of particles.

FIG. 2 shows very schematically the construction of an optical apparatus in accordance with the present invention for measuring the roughness of the surface of a body.

Figure 3:
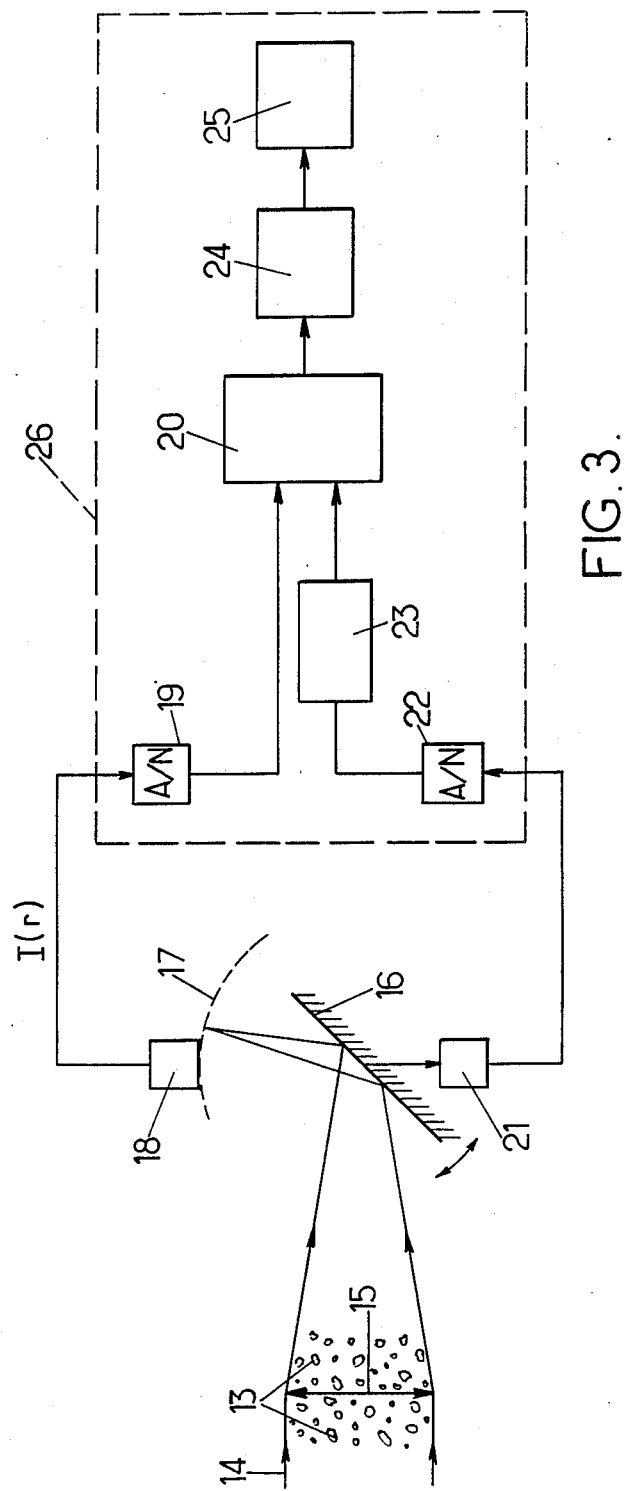
FIG. 3 is a very schematic representation of an electronic apparatus in accordance with the present invention for measuring the granulometry of a cloud of particles.

In accordance with the present invention, the zone to be analysed is illuminated by means of a light beam emitted by a coherent light source, this light beam passing through the cloud of particles whose granulometry it is desired to measure or being reflected by the surface whose roughness it is desired to know.

This coherent light beam then reaches a convergent lens which provides a diffraction pattern of the cloud of particles or of the rough surface.

This diffraction pattern is then multiplied in intensity by a function f(r) such that $$A(r^{1.5} + Br_o^4) < f(r) < A(r^4 + Br_o^4)$$

such multiplication being able to be made electronically by means of an electronic computer or purely optically by means which will be discussed further on.

In the above expressions, A is an apparatus constant which may be calculated from Fraunhofer's diffraction theory and from the response of the detector used: in the case of a purely optical process, the coefficient A is determined in practice by calibrating the apparatus on a previously known diffracting object, such as a single hole; B is a constant characterizing the transmission power of the amplitude or phase spatial filter whose value is between 0 (central opaque mask) and 0.1; r is the distance measured in the focal plane of the convergent lens with respect to te optical axis thereof; and $r_o$ is the maximum useful radius of the spatial filter.

The result of this intensity multiplication then undergoes a reverse Fourier transform, either electronically by means of an electronic computer using the appropriate algorithms known to a man skilled in the art, or purely optically as explained further on. Thus, a granulometry spectrum is obtained which may be divided into classes of particles or else, depending on the case, a roughness spectrum of the surface.

Although it provides a result having very good accuracy which is advantageous for some applications, the electronic procedure using electronic mathematical computing means has however the drawbacks of slowness in processing the data and obtaining the result, and so accordingly the impossibility of following an evolutive phenomenon in real time, and also the excessive cumbersomeness of the equipment used which limits its conditions of use (impossibility of embarking the equipment in a vehicle such as a missile).

This is why the purely optical method, which eliminates all these drawbacks while providing results of sufficient accuracy for current applications, seems to be the most advantageous and two examples of purely optical apparatus, one for measuring the granulometry of a cloud of particles and the other for measuring the roughness of a surface, without contact and in real time, will now be described more particularly in greater detail with reference to FIGS. 1 and 2.

The apparatus shown in FIGS. 1 and 2 have common parts and, in these figures, identical elements are designated by the same numerical references.

Referring first of all to FIG. 1, the apparatus for measuring the granulometry of a cloud of particles, designated generally by the reference 1, comprises a coherent light source 2 whose radiation may be taken up by a lens 3 so as to form a beam with parallel rays 4 which is directed on the cloud of particles 5 to be analysed and passes therethrough.

Referring now to FIG. 2, the apparatus for measuring the roughness of the surface of a body, designated as a whole by the reference 6, comprises a coherent light source 2 whose radiation is taken up by a lens 3 so as to form a beam with parallel rays 4 which is directed on the surface 7 of body 8 to be analysed.

Beam 4, after passing through the cloud of particles 5 in apparatus 1 or after being reflected by surface 7 in apparatus 6, reaches a first convergent lens which forms, optically, a diffraction pattern of the cloud or of the surface respectively.

In the image focal plane of the first lens 9 there is disposed an optical amplitude or phase spatial filtering device 10 which optically multiplies, in intensity, the diffraction pattern formed by the first lens.

The optical filtering device 10 may be a filter whose opacity decreases the further away it is from the optical axis of the system, and the light intensity passing through it follows the above law f(r). The centre of this filter may possibly be blackened and totally opaque (B=0 in the above formula).

The optical filtering device 10 may also be formed by an opaque mask whose area between two radii r and r+dr increases so that the light intensity passing through the corresponding ring increases in accordance with the law f(r).

Finally, a second convergent lens whose object focal point is situated at the image focal point of the first lens provides optically the appropriate Fourier transform of the optical signal and forms the granulometry (for apparatus 1) or roughness (for apparatus 6) spectrum in its image focal plane 12.

The granulometry or roughness spectrum thus collected in the focal plane 12 may be used by any appropriate means known by a man skilled in the art and outside the scope of the present invention.

Thus, an apparatus adapted in accordance with the present invention makes it possible to obtain the granulometry spectrum of a cloud of particles or the roughness spectrum of the surface of a body, and this continuously in real time and without contact, using purely optical equipment, so relatively compact, light and robust, which may if required be readily taken on board a vehicle such as a missile or a rocket and which gives satisfactory measurement accuracy for most of the types of measurement envisaged.

In FIG. 3 is shown schematically an electronic apparatus providing the granulometry spectrum of a cloud of particles 13. A coherent light beam 14 is directed on the cloud of particles 13 and is focussed by a convergent lens 15 (particles 13 being situated either before or after lens 15). The beam from lens 15 is taken up and reflected by a swinging mirror 16. The diffraction pattern may then be moved over a circular path 17 in which is disposed a fixed detector 18, such as a photomultiplier, sensitive to the light of the coherent beam and delivering an analog electric signal I (r). This analog signal is processed by an A/D converter 19 before being applied to a first input of a multiplier device 20.

The angular movement of mirror 16 is detected by an angular position detector 21 delivering an analog electric signal which is processed by an A/D converter 22. The digital output signal from the latter is multiplied by the above function f(r) in a multiplier device 23, whose output is connected to a second input of the multiplier device 20.

The output signal from the multiplier 20, representative of the product I(r)·f(r), is then applied to a spectrum analyser 24 using for example the known fast Fourier transform algorithms which delivers a granulometry or surface roughness spectrum which is displayed by a display device 25.

Of course, all the part for processing the electric signals, shown in FIG. 3 in the broken line box 26, may be provided by a computer.

It will be noted that the computations may also be provided using purely analog multiplier devices or spectrum analysers. However, in this case the accuracy is not as good as that obtained by passing through an A/D conversion of the data.

The apparatus shown in FIG. 3 may be suitable for all applications in which high computing accuracy is required for determining the granulometry spectrum, but in which speed in obtaining the result is not required, since this apparatus does not operate in real time.

Following which and as is evident from the foregoing, the invention is in no wise limited to those of its modes of application and embodiments which have been more especially considered; it embraces, on the contrary, all variants thereof.

I claim:

1. Method for the contactless measurement in real time of the granulometry of a cloud of particles or of the roughness of a surface characterized in that:
   a diffraction pattern is formed of the cloud of particles or of the surface of the body, by means of a convergent lens,
   this diffraction pattern is multiplied, in intensity, by a function f(r) such that $$A(r^{1.5}+Br_o^4)<f(r)<A(r^4+Br_o^4)$$

with
   A=constant determined by calibration
   B=constant: $o<B<0.1$
   r=distance measured in the focal plane of the lens with respect to the optical axis thereof,
   $r_o$ =maximum useful radius of the spatial filter,
   and a reverse Fourier transform is carried out on the result of this multiplication, whose result forms the desired spectrum of the granulometry of the cloud of particles or the desired spectrum of the roughness of the surface.

2. Method according to claim 1, characterized in that the function f(r) is zero or less than the preceding value in the range $o<r<r_o/4$.

3. Method according to claim 1, characterized in that the multiplication in intensity of the diffraction pattern by the function f(r) and the reverse Fourier transform are carried out using electronic computing means.

4. Method according to claim 1, characterized in that the diffraction pattern is multiplied optically, in intensity, by an optical amplitude or phase spatial filter device situated in the image focal plane of said convergent lens, and in that the granulometry or roughness spectrum is formed optically by means of a second convergent lens whose object focal point is situated at the image focal point of the first convergent lens.

5. An apparatus for measuring the granulometry of a cloud of particles or of the roughness of a surface in real time and without contact, characterized in that it comprises:
   a convergent lens (9, 15) adapted for forming a diffraction pattern of the cloud of particles or of the surface,
   multiplier means (10, 20) adapted for multiplying this diffraction pattern, in intensity, by a function f(r) such that $$A(r^{1.5}+Br_o^4)<f(r)<A(r^4+Br_o^4)$$

with
   A=constant determined by calibration of the apparatus
   B=constant: $o<B<0.1$ r = distance measured in the focal plane of the lens with respect to the optical axis thereof, $r_o$ = maximum useful radius of the spatial filter, and means (11, 24) adapted for carrying out a reverse Fourier transform on the result of the above intensity multiplication, whose result forms the desired spectrum of the granulometry of the cloud of particles or the desired spectrum of the roughness of the surface.

6. Apparatus according to claim 5, characterized in that a central opaque mask is provided, the function $f(r)$ then being zero or less than the preceding value in the range $0 < r < r_o/4$.

7. Apparatus according to claim 5, characterized in that the intensity multiplying means (20) and the means providing the reverse Fourier transform (24) are in the form of electronic computers.

8. Apparatus according to claim 5, characterized in that the means providing the reverse Fourier transform comprise a second convergent lens (11) disposed so that its object focal point is situated at the image focal point of the first lens, and in that the intensity multiplier means comprise an optical amplitude or phase spatial filtering device (10) situated at the image focal point of the first lens and at the object focal point of the second lens, whereby, when the apparatus receives electromagnetic radiation having passed through the cloud of particles or been reflected by the surface, the spectrum of the granulometry of the cloud of particles or of the roughness of the surface is formed in the image focal plane (12) of the second lens (11).

9. Apparatus according to claim 8, characterized in that the optical filtering device is a filter whose opacity decreases the further it is removed from the optical axis of the system.

10. Apparatus according to claim 8, characterized in that the optical filtering device is an opaque mask whose area between two radii increases so that the intensity passing through this annular surface increases in accordance with the above mentioned law $f(r)$.

* * * * *